United States Patent [19]

Hogg

[11] 3,987,391
[45] Oct. 19, 1976

[54] METHOD AND APPARATUS FOR CORRECTING TOTAL PARTICLE VOLUME ERROR DUE TO PARTICLE COINCIDENCE

[75] Inventor: Walter R. Hogg, Miami Lakes, Fla.

[73] Assignee: Coulter Electronics, Inc., Hialeah, Fla.

[22] Filed: Dec. 2, 1974

[21] Appl. No.: 528,645

[52] U.S. Cl. ............................................ 324/71 CP
[51] Int. Cl.² ......................................... G01N 27/00
[58] Field of Search ............. 324/71 CP; 235/92 PC, 235/92 PL

[56] References Cited
UNITED STATES PATENTS

| | | | |
|---|---|---|---|
| 3,439,267 | 4/1969 | Coulter et al. | 324/71 CP |
| 3,473,010 | 10/1969 | Bloomfield et al. | 324/71 CP X |
| 3,737,633 | 6/1973 | Collineau | 324/71 CP X |

Primary Examiner—John K. Corbin
Assistant Examiner—Rolf Hille
Attorney, Agent, or Firm—Silverman & Cass, Ltd.

[57] ABSTRACT

In an apparatus which develops output signal data, a portion of a liquid containing particles is caused to flow through a sensing zone. Ideally the particles go through one at a time. Each particle sensed generates a particle signal having an amplitude proportional to the size or volume of the particle. The particle signal is utilized for producing the output signal data. The output signal data is a measure of the total volume of particulate matter in a quantity of liquid containing particles and is subject to error due to the occasional simultaneous presence of particles in the sensing zone which is termed coincidence.

An error correction signal is also developed by the apparatus which varies in accordance with the repetition rate of particles passing through the sensing zone. The error correction signal is employed to correct the output signal data which is subject to error due to particle coincidence.

20 Claims, 2 Drawing Figures

METHOD AND APPARATUS FOR CORRECTING TOTAL PARTICLE VOLUME ERROR DUE TO PARTICLE COINCIDENCE

CROSS REFERENCE TO RELATED PATENTS

This application is related to U.S. Pat. No. 3,757,213 entitled "Particle Size Analyzing Apparatus and Method Using Threshold Level Control", which patent is hereby incorporated by reference into this application.

BACKGROUND OF THE INVENTION

In the apparatus identified in the above noted U.S. Pat. No. 3,757,213, particles in a particulate system are passed through a Coulter type apparatus. Each particle causes a particle pulse to be developed whose amplitude is proportional to the size of the particle producing it. Those pulses having amplitudes which exceed a preselected threshold level are applied to a voltage to charge converter. The resulting charges produced from all of the applied signals are accumulated in a device such as an integrating circuit, and provide an output voltage which is proportional to the total amplitudes of all applied signals. Accumulated for a given number of the particle pulses, the output voltage is proportional to the mean particle volume. Accumulated for a given volume of test suspension which is allowed to flow through the aperture of the Coulter type apparatus, the first mentioned output voltage is proportional to the ratio of total particulate volume to diluent volume.

In the Coulter type apparatus such as is described in U.S. Pat. Nos. 2,656,508; 2,985,830; and 3,259,842; a significantly important portion of such apparatus is the minute scanning aperture or scanning ambit relative to or through which pass and are detected, single particles. The particles pass through the aperture at a rate often well in excess of one thousand per second. Each particle, as it passes through the scanning aperture will cause a particle pulse to be developed whose amplitude is propportional to its size, it being understood that "size" as used herein always refers to the volume of material or substance in a particle. Because of the dimensions of the scanning aperture, and concentration of the particles in the suspension, etc., frequently there results a coincidence of two particles in the scanning ambit. As a result, the response is as if only one particle, not two were scanned. This response is a pulse whose amplitude is not necessarily representative of the volumes of the two particles in the scanning ambit, so that the output voltage accumulated by the apparatus, instead of being proportional to the total amplitudes of all the applied signals, will contain errors introduced as a result of coincidence of particles in the scanning ambit.

It has been found that the amount of error introduced as a result of coincidence of particles in the scanning ambit is related to the frequency or rate at which the particles pass through the scanning ambit or aperture. That is, the higher the rate of passage of particles through the scanning ambit, the greater the coincidence error. It is, therefore, desirable to correct the error in output voltage which occurs as a result of coincidence in accordance with a correction factor that is related to the rate at which particles pass through the scanning ambit, in order that higher concentrations of particles may be used, with resultant savings of time.

SUMMARY OF THE INVENTION

In practicing this invention there is provided an apparatus for producing output signal data related to the total volume of particulate matter in a quantity of liquid containing particles. In the apparatus, a portion of the liquid containing particles is caused to flow through a sensing zone or scanning ambit of a Coulter type apparatus. As each particle passes through the sensing zone, it generates a particle signal having an amplitude proportional to the size or volume of the passed particle. This particle signal is utilized for producing the output signal data. The output signal data is subject to error due to coincidence of particles in the sensing zone. In the apparatus, an error correction device is provided which is operative to vary in a predetermined manner the output signal data to correct the data for total volume error due to coincidence of particles. In the preferred embodiment, the error correction means is operative to vary the output signal data in accordance with the repetition rate of the particle signals.

DETAILED DESCRIPTION OF THE DRAWINGS

When a circuit corresponds to a circuit in the incorporated patent the circuit number in this application will be followed by an *a* subscript in order to simplify crossreferencing to the incorporated patent.

For a complete understanding of the purpose and the operation of the Particle Size Analyzing Apparatus and Method Using Threshold Level Control, reference is to be made to the patent incorporated by reference. However, for purposes of a more clear understanding of this application, some explanation of the circuitry shown and described in the incorporated patent, and operatively associated with the error correction circuitry, is in order. The explanation will be given with respect to FIG. 1 of this application.

Figure 2:
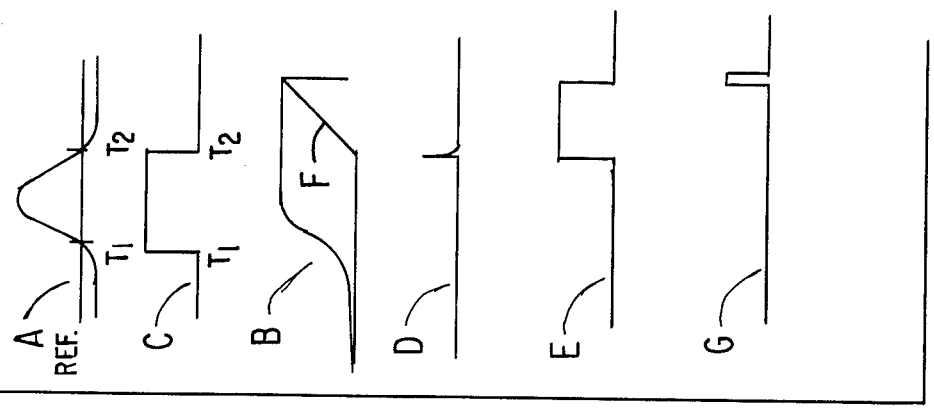
FIG. 2 shows the waveforms at various points of the block diagram shown in FIG. 1.
Figure 1:
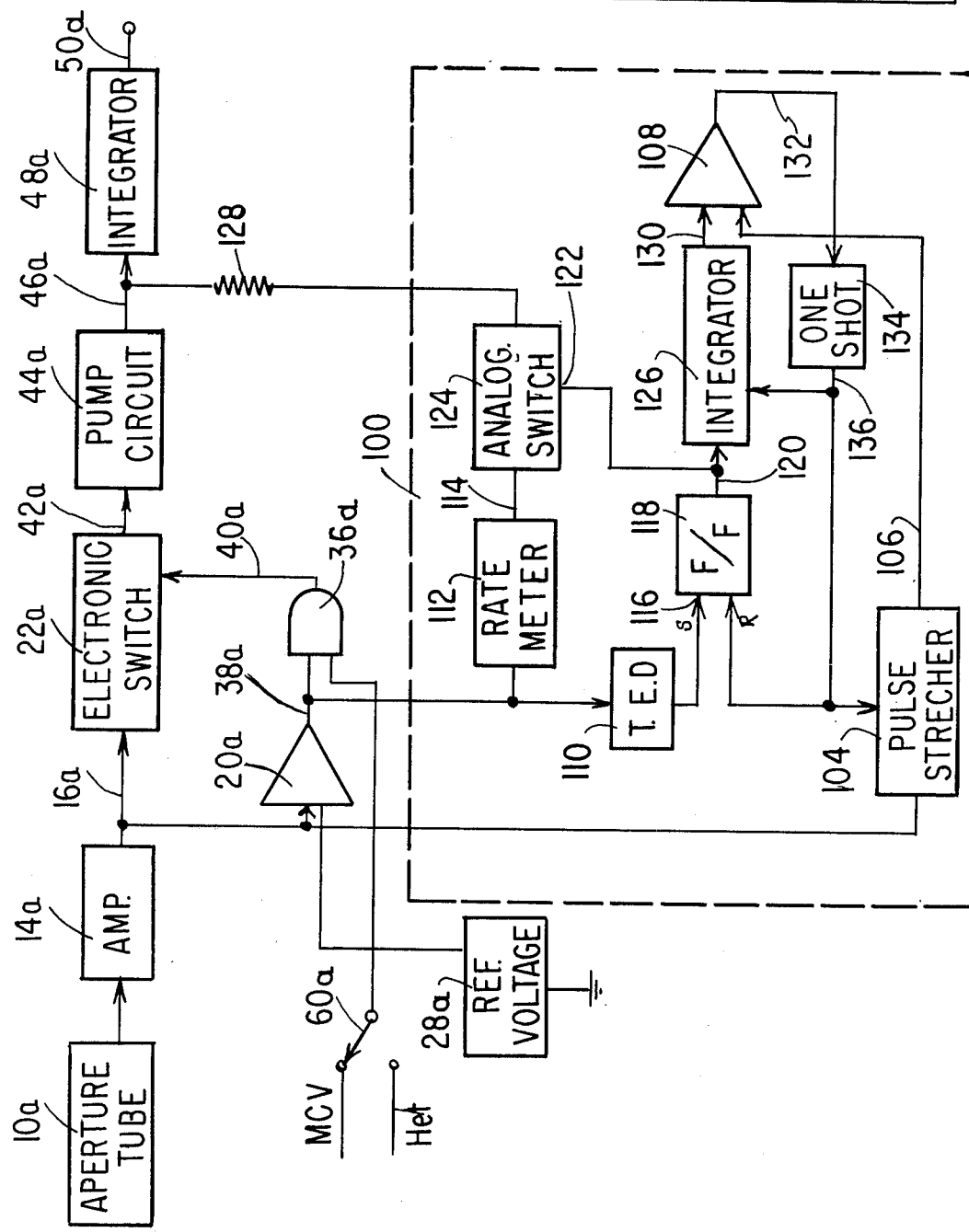
FIG. 1 is a block diagram of the error correction circuit of this invention shown incorporated into a portion of FIG. 1 of the patent which is incorporated by reference.

In FIG. 1, particles in a particulate system are passed through a Coulter type aperture tube 10a. An electric current also is passed through the aperture tube 10a. Particle pulses are produced as a result of the modulation of this current by passage of the particles through the aperture tube 10a. Each pulse amplitude is proportional to the size or volume of the pulse producing particle. These particle pulses are amplified by amplifier 14a and coupled to a comparator 20a, via conductor 18a. One such amplified pulse is shown in FIG. 2, waveform A. If the particle pulse exceeds a preset level or threshold, as determined by voltage source 28a, comparator 20a will develop a comparator signal such as shown in FIG. 2, waveform C which is coupled to an input of AND gate 36a by conductor 38a. This pulse is present only during the period that the amplified pulse exceeds the preset threshold level. The pulse shown in FIG. 2, waveform A exceeds this threshold during the period exceeding from time $T_1$ to $T_2$. AND gate 36a will develop an output signal in response to the comparator signal which is coupled via conductor 40a to electronic switch 22a for operating switch 22a to allow the particle pulses from amplifier 14a to pass through electronic switch 22a to a pump circuit 44a. Pump circuit 44a converts each pulse to a charge which is coupled via conductor 46a to integrator 48a which accumulates the charges. Integrator 48a in effect adds all of the signals passed by the electronic switch 22a, and the voltage level at its output terminal 50a at any time represents the accumulated signals. If the signals are accumulated for a predetermined number of particles, the voltage level will also represent the mean particle volume. It is assumed that the count of the number of particles accumulated also has been corrected for coincidence loss by some arrangement such as is described in copending patent application Ser. No. 441,752 filed Feb. 12, 1974 so that the mean particle volume can be obtained based upon a correct particle count. Because of particle coincidence the voltage or output signal data appearing at output terminal 50a, will be slightly in error if samples having high particle concentrations are employed.

In order to eliminate the coincidence error in the output signal data, a coincidence error correction circuit, shown in dotted lines and identified generally by the number 100 is employed. The amplified particle pulse such as shown in FIG. 2, waveform A, also is coupled by conductor 18a to a pulse stretcher 104. Pulse stretcher 104 will develop an output signal voltage that increases in amplitude to a voltage which is equal to or is related to the amplitude of the particle pulse developed at the output of amplifier 14a. Accordingly the output voltage is equal or related to the particle size. Once the maximum amplitude of the pulse has been reached, pulse stretcher 104 will maintain that maximum amplitude. The stretched signal output developed by pulse stretcher 104 is coupled by a conductor 106 to the first input of a second comparator 108. The stretched signal output developed on conductor 106, and produced by the pulse shown in FIG. 2, waveform A, is shown in FIG. 2, waveform B.

In addition to coupling the output of comparator 20a to AND gate 36a as previously noted, the output of comparator 20a is also coupled to a trailing edge detector 110 and a rate meter 112, both in coincidence correction circuit 100. Rate meter 112 is of the type commonly known in the art which will develop an output voltage at conductor 114 that varies in accordance with the repetition rate of the pulses coupled thereto. Accordingly, the voltage at conductor 114 will be at some amplitude which is determined by the repetition rate over a preceding predetermined time period of pulses such as shown in FIG. 2, waveform C.

Trailing edge detector 110 responds to the trailing edge of each pulse developed by comparator 20a and develops a pulse which is coupled to the set input 116 of a bistable multivibrator 118. The pulse developed by trailing edge detector 110 in response to the signal shown in FIG. 2, waveform C is shown in FIG. 2, waveform D. Bistable multivibrator 118, better known as a "flip-flop", responds to the set pulse at input 116 and develops a control signal pulse of fixed amplitude at its output. The control signal produced by flip-flop 118 in response to waveform D is shown in FIG. 2, waveform E. This pulse is coupled by a conductor 120 to the control input 122 of analog switch 124 and to the input of an integrator 126. Analog switch 124 operates in response to the control signal coupled to input 122 to couple the voltage developed by rate meter 112 at conductor 114 to summing resistor 128. Summing resistor 128 converts the voltage to a charging current whose amplitude is proportional to the amplitude of the voltage developed by rate meter 112. As the rate meter voltage amplitude varies in accordance with the repetition rate of particle pulses, the charging current amplitude will vary with the particle pulse repetition rate. The charging current is coupled from summing resistor 128 to integrator 48a in the same mnner as the charging current developed by pump circuit 44a, and is accumulated in integrator 48a along with the currents from pump circuit 44a.

The pulses developed by flip-flop 118 such as for example the pulse of FIG. 2, waveform E, are also coupled to integrator 126. Integrator 126 will integrate each pulse coupled thereto and develop an integration voltage such as shown in FIG. 2, waveform F. Waveform F is superimposed upon waveform B in order to simplify certain portions of this explanation. The integration voltage developed by the integrator 126 is coupled via conductor 130 to the second input of comparator 108. As previously noted the voltage amplitude at the first input of comparator 108 is equal to or related to the particle size. When the voltage developed by integrator 126 reaches and exceeds the voltage developed at the output of pulse stretcher 106, comparator 108 will change states and develop a comparison signal at its output which is coupled by the conductor 132 to a monostable multivibrator 134, more commonly known as "one shot". One shot 134 will change states in response to the comparison signal and develop a pulse for a very short period of time as shown in FIG. 2, waveform G. This pulse is coupled via conductor 136 to the reset inputs of integrator 126, flip-flop 118 and pulse stretcher 104 resetting all three devices. With flip-flop 118 reset, the pulse developed at conductor 120 and coupled to control input 122 of analog switch 124 terminates as shown in FIG. 2, waveform E, thus terminating the voltage coupled from rate meter 112 to summing resistor 128. Accordingly, the charging current coupled to integrator 48a for providing the volume coincidence correction to the voltage developed at conductor 50a is terminated. As flip-flop 118 is set, or on for a time period which is related to the size of particles the charging current duration is related to particle size.

In the preferred embodiment, the component values employed in rate meter 112, integrator 126 and current limiting resistor 128 are determined via trial and error method. Specifically, a known volume of particulate matter in a quantity of liquid is passed through the apparatus and the voltage representing the volume of particulate matter is noted. The particulate concentration is then changed, changing the total volume of particulate matter in the sample. Preferably, the dilution is doubled, thus halving the concentration. The sample then is again passed through the apparatus and the total voltage representing the total volume of particulate matter is noted. If the component values selected for rate meter 112, integrator 126 and charging resistor 128 are correct, the voltage for the diluted sample should be one-half the voltage developed due to the original sample.

What it is desired to be secured by Letters Patent of the United States is:

1. A method of ascertaining the total volume of particulate matter suspended in a quantity of liquid and for correcting error in ascertaining said total volume including the steps of:

A. passing the quantity of liquid through a sensing zone where each particle generates a particle signal having an amplitude which is directly proportional to the size of the individual particle sensed, B. converting each signal into an electrical quantity which is directly related to the amplitude of said signal without regard to its duration and which is capable of being accumulated, C. accumulating all of the electrical quantities generated by particles sensed in said quantity of liquid, D. deriving at least one output which is proportional to the total accumulated electrical quantities and hence also is proportional to the total volume of particulate matter so suspended in said quantity of liquid, E. developing an error correction signal having an amplitude which varies in accordance with the repetition rate of the particles passing through the sensing zone, and F. varying the output signal in accordance with said error correction signal.

2. The method of claim 1 wherein the step of developing said error correction signal includes the step of developing a repetition rate signal which varies in amplitude in accordance with the repetition rate of particle signals and coupling said repetition rate signal to said accumulating means for a predetermined period in response to each particle pulse.

3. The method of claim 2 in which said predetermined period is a function of particle size.

4. The method of claim 1 wherein said step of developing an error correction signal includes:

A. developing a first signal in response to each particle pulse having a duration related to the particle pulse amplitude, B. converting said repitition rate signal into a second electrical quantity which is capable of being accumulated, said quantity varying in amplitude in accordance with said repetition rate signal and having a duration substantially equal to said first signal duration, and C. accumulating said second electrical quantities with said electrical quantities for varying said output signal.

5. The method of claim 4 wherein the step of developing said first signal includes the step of:

A. measuring the maximum amplitude of each particle pulse,

B. developing said first signal in response to passage of each pulse,

C. integrating each said first signal to develop an integration signal,

D. terminating said first signal when said integration signal exceeds said maximum amplitude of said particle pulse.

6. In an apparatus for providing output signal data representing the total volume of particulate matter in a quantity of liquid wherein a portion of the liquid is caused to flow through a sensing zone and each particle sensed generates a particle signal having an amplitude proportional to the size of the particle, which particle signal is utilized for producing the output signal data, and wherein said output signal data is accumulated in an accumulation means and is subject to error due to coincidence of particles in the sensing zone, the improvement comprising, error correction means operative to vary in a predetermined manner the output signal data to correct said data for total volume error due to coincidence of particles, said error correction means including rate detection means operative to develop a repetition rate signal varying in amplitude in accordance with the repetition rate of said particles, said output signal data varying in accordance with said repetition rate signal.

7. The apparatus of claim 6 wherein said error correction means is operative to develop a correction signal varying in amplitude in accordance with the size and repetition rate of said particle signals, said accumulation means being coupled to said error correction means and responsive to said correction signal to vary said output signal data to correct for total volume error due to coincidence of particles.

8. The apparatus of claim 7 wherein said accumulation means sums said output signal data and said error correction signal.

9. The apparatus of claim 6 wherein said control means coupled to said rate detection means and operative in response to said particle pulses and said repetition rate signal to develop a correction signal, said accumulation means being coupled to said control means and responsive to said repetition rate signal to vary said output signal data to correct for total volume error.

10. The apparatus of claim 9 wherein said control means includes, pulse amplitude means responsive to each particle signal to generate a duration signal having a duration related to said particle signal amplitude, said control means operative in response to said duration signal to develop said correction signal having an amplitude related to the amplitude of said repetition rate signal and a duration of said duration signal.

11. The apparatus of claim 10 wherein said pulse amplitude means includes maximum amplitude determining means coupled to said sensing zone and operative to develop a maximum amplitude signal related to the maximum amplitude of each particle signal, timing means coupled to said maximum amplitude determining means and operative in response to passage of each particle pulse to develop said duration signal having a duration which varies in accordance with the maximum amplitude of said maximum amplitude signal.

12. The apparatus of claim 11 wherein said maximum amplitude determining means is a pulse stretcher.

13. The apparatus of claim 11 wherein said timing means includes circuit means coupled to said maximum amplitude determining means and operative in response to passage of each particle pulse to develop said duration signal, integration means coupled to said circuit means and operative to integrate said duration signal and develop an integration signal, comparison means coupled to said integration means, and maximum amplitude determining means and operative in response to said integration signal exceeding said maximum amplitude signal to develop a termination signal for resetting said circuit means integration means and maximum amplitude determining means whereby said duration signal is terminated.

14. The apparatus of claim 13 wherein said control means include switch means coupled to said rate detection means and said timing means and operative in response to said repetition rate signal amplitude to develop said correction signal having an amplitude related to the amplitude of said repetition rate signal and a duration of said duration signal.

15. The apparatus of claim 13 wherein said circuit means include a trailing edge detector operative in response to the trailing edge of each particle pulse to develop a trailing edge signal, and a bistable multivibrator coupled to said trailing edge detector and operative in response to said trailing edge signal to develop said duration signal.

16. Apparatus for producing output signal data representing the total volume of particulate matter in a quantity of liquid containing said particulate matter, utilizing the output signals from a particle analyzing device wherein the quantity of liquid containing said particulate matter is caused to flow through a sensing zone including an electric current path of small dimensions wherein each particle sensed generates a particle signal having an amplitude proportional to the size of the particle sensed, said apparatus comprising:
   A. means for converting each signal as it occurs into an electrical quantity directly proportional to the amplitude of said signal without regard to its duration and capable of being accumulated,
   B. means for accumulating said quantities,
   C. means responsive to the total accumulated quantity providing an output signal proportional to said total quantity,
   D. means for controlling the operation of said accumulation means, and
   E. error correction means operative in a predetermined manner to vary the output signal to correct said output signal for its total volume error due to coincidence of particles, said error correction means including rate detection means coupled to said means for converting each signal as it occurs into an electrical quantity and being operative to develop a repetition rate signal which varies in amplitude in accordance with the repetition rate of particle signals, said output signal varying in accordance with said repetition rate signal amplitude.

17. The apparatus of claim 16 wherein said error correction means include control means coupled to said rate detection means and operative in response to said particle pulses and said repetition rate signals to develop error correction signals, said means for accumulating said quantities being coupled to said control means and responsive to said correction signal to vary said output signal data to correct for total volume error.

18. The apparatus of claim 16 wherein said control means includes, pulse amplitude means responsive to each particle signal to generate a duration signal having a duration related to said particle signal amplitude, said control means operative in response to said duration signal to develop said correction signal having an amplitude related to the amplitude of said reptitition rate signal and a duration of said duration signal.

19. The apparatus of claim 16 wherein said quantity of liquid containing said particulate matter is a quantity of liquid containing a predetermined number of particles to be sensed.

20. The apparatus of claim 16 wherein said quantity of liquid containing said particulate matter is a predetermined volume of liquid.

* * * * *